US00PP33059P2

(12) United States Plant Patent
van der Meer

(10) Patent No.: US PP33,059 P2
(45) Date of Patent: May 11, 2021

(54) ***ASTILBE* PLANT NAMED 'MOCCACHINO'**

(50) Latin Name: **(*Astilbe japonica* x *A. arendsii*) X *Astilbe thunbergii***
Varietal Denomination: Moccachino

(71) Applicant: Hans van der Meer, Nieuwe Wetering (NL)

(72) Inventor: Hans van der Meer, Nieuwe Wetering (NL)

(73) Assignee: COMPASS PLANTS B.V., Hillegom (NL)

( * ) Notice: Subject to any disclaimer, the term of this patent is extended or adjusted under 35 U.S.C. 154(b) by 0 days.

(21) Appl. No.: 16/974,010

(22) Filed: Sep. 5, 2020

(51) Int. Cl.
*A01H 6/80* (2018.01)
*A01H 5/02* (2018.01)

(52) U.S. Cl.
USPC ..... Plt./407

(58) Field of Classification Search
USPC ..... Plt./407
See application file for complete search history.

(56) References Cited

PUBLICATIONS

PLUTO Plant Variety Database Dec. 15, 2020.*

* cited by examiner

*Primary Examiner* — Annette H Para
(74) *Attorney, Agent, or Firm* — C. Anne Whealy

(57) ABSTRACT

A new and distinct cultivar of *Astilbe* plant named 'Moccachino', characterized by its broadly upright and mounding plant habit; vigorous growth habit; dark green-colored leaves; freely and uniformly flowering habit; white-colored flowers arranged in large showy inflorescences and borne on strong reddish-colored peduncles; and good container and garden performance.

2 Drawing Sheets

Botanical designation: (*Astilbe japonica* x *A. arendsii*) X *Astilbe thunbergii.*
Cultivar denomination: 'MOCCACHINO'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Astilbe*, botanically known as (*Astilbe japonica* x *A. arendsii*) X *Astilbe thunbergii* and hereinafter referred to by the name 'Moccachino'.

The new *Astilbe* plant is a product of a planned breeding program conducted by the Inventor in Nieuwe Wetering, The Netherlands. The objective of the breeding program was to create new uniform and freely flowering *Astilbe* plants with attractive leaf and flower coloration.

The new *Astilbe* plant originated from an open-pollination in 2014 in Nieuwe Wetering, The Netherlands, of *Astilbe japonica* X *A. arendsii* 'Cappuccino', disclosed in U.S. Plant Pat. No. 24,940, as the female, or seed, parent with an unknown *Astilbe thunbergii* seedling selection as the male, or pollen, parent. The new *Astilbe* plant was discovered and selected by the Inventor as a single flowering plant from within the progeny of the stated open-pollination in a controlled greenhouse environment in Nieuwe Wetering, The Netherlands during the summer of 2015.

Asexual reproduction of the new *Astilbe* plant by vegetative divisions in a controlled nursery environment in Nieuwe Wetering, The Netherlands since December, 2015, has shown that the unique features of this new *Astilbe* plant are stable and reproduced true to type in successive generations.

SUMMARY OF THE INVENTION

Plants of the new *Astilbe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Moccachino'. These characteristics in combination distinguish 'Moccachino' as a new and distinct *Astilbe* plant:

1. Broadly upright and mounding plant habit.
2. Vigorous growth habit.
3. Dark green-colored leaves.
4. Freely and uniformly flowering habit.
5. White-colored flowers arranged in large showy inflorescences and borne on strong reddish-colored peduncles.
6. Good container and garden performance.

Plants of the new *Astilbe* differ primarily from plants of the female parent, 'Cappuccino', in the following characteristics:

1. Plants of the new *Astilbe* are larger than and not as compact as plants of 'Cappuccino'.
2. Inflorescences of plants of the new *Astilbe* are more arching than and not as upright as inflorescences of plants of 'Cappuccino'.

Plants of the new *Astilbe* can be compared to plants of *Astilbe thunbergii* 'Straussenfeder', not patented. In side-by-side comparisons, plants of the new *Astilbe* and 'Straussenfeder' differ primarily in the following characteristics:

1. Plants of the new *Astilbe* are shorter than plants of 'Straussenfeder'.
2. Plants of the new *Astilbe* are more freely flowering than plants of 'Straussenfeder'.
3. Flowers of plants of the new *Astilbe* are white in color whereas flowers of plants of 'Straussenfeder' are pale pink in color.
4. Inflorescences of plants of the new *Astilbe* are denser than and not as open as inflorescences of plants of 'Straussenfeder'.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet is a side perspective view of a typical flowering plant of 'Moccachino' grown in a container.

The photograph on the second sheet is a close-up view of typical inflorescences of 'Moccachino'.

DETAILED BOTANICAL DESCRIPTION

The aforementioned photographs and following observations, measurements and values describe plants grown during the spring and early summer in ground beds and 30-cm containers in an outdoor nursery in Nieuwe Wetering, The Netherlands and under cultural practices typical of commercial *Astilbe* production. During the production of the plants, day temperatures ranged from 15° C. to 32° C. and night temperatures ranged from 8° C. to 18° C. Plants were two years old when the photographs and description were taken. In the following description, color references are made to The Royal Horticultural Society Colour Chart, 2015 Edition, except where general terms of ordinary dictionary significance are used.

Botanical classification: (*Astilbe japonica* x *A. arendsii*) X *Astilbe thunbergii* 'Moccachino'.

Parentage:

*Female, or seed, parent*.—*Astilbe japonica* X *A. arendsii* 'Cappuccino', disclosed in U.S. Plant Pat. No. 24,940.

*Male, or pollen, parent*.—Unknown *Astilbe thunbergii* seedling selection, not patented.

Propagation:

*Type*.—By vegetative divisions.

*Time to initiate roots*.—About three weeks at temperatures about 20° C.

*Root description*.—Thick, fleshy; typically brown in color, actual color of the roots is dependent on substrate composition, water quality, fertilizer type and formulation.

*Rooting habit*.—Freely branching; dense.

Plant description:

*Plant form and growth habit*.—Herbaceous perennial; broadly upright and mounding plant form with inflorescences held above the foliar plane; overall plant shape, flattened globular; flowering stems and leaves basal; freely flowering with about 32 basal branches per plant, dense and bushy; vigorous growth habit; and freely and uniformly flowering habit.

*Growth rate*.—Moderately rapid to rapid; from divisions, about three months are required to produce fully-grown flowering plants in containers.

*Plant height* (*soil level to top of foliar plane*).—About 45.8 cm.

*Plant height* (*soil level to top of inflorescences*).—About 78 cm.

*Plant width* (*spread*).—About 66 cm.

*Stem description*.—Length: About 42.1 cm. Diameter: About 4 mm. Internode length: About 16.2 cm. Strength: Strong. Aspect: Erect to about 5° from vertical. Texture and luster: Sparsely pubescent; slightly glossy. Color, developing: Close to 177B. Color, developed: Close to 178A; surfaces not exposed to sunlight, close to 172A to 172B; at the internodes, close to 178A.

Leaf description:

*Arrangement*.—Alternate; biternately compound; on average, about 29 leaflets per leaf.

*Leaf length* (*excluding petiole*).—About 20.3 cm.

*Leaf width*.—About 20.2 cm.

*Terminal leaflet length*.—About 5.2 cm.

*Terminal leaflet width*.—About 3 cm.

*Lateral leaflet length*.—About 3.8 cm.

*Lateral leaflet width*.—About 2 cm.

*Leaf shape, in outline*.—Broadly ovate to broadly deltoid.

*Leaflet shape*.—Ovate to elliptic.

*Leaflet apex*.—Acuminate to apiculate.

*Leaflet base*.—Short attenuate to narrowly obtuse.

*Leaflet margin*.—Biserrate.

*Leaflet texture and luster, upper surface*.—Moderately pubescent; moderately glossy.

*Leaflet texture and luster, lower surface*.—Moderately pubescent; slightly glossy.

*Leaflet venation pattern*.—Pinnate.

*Leaflet color*.—Developing leaflets, upper surface: Close to 147A tinged with close to 200C. Developing leaflets, lower surface: Close to 147A to 147B tinged with darker than 197A. Fully expanded leaflets, upper surface: Close to between NN137A and 147A; venation, close to 148B, proximally, midvein strongly tinged with close to 182B. Fully expanded leaflets, lower surface: Close to 147B; venation, close to 182A.

*Leaf petiole length*.—About 9.7 cm.

*Leaf petiole diameter*.—About 2 mm.

*Leaf and leaflet petiole strength*.—Strong.

*Leaf and leaflet petiole texture and luster, upper and lower surfaces*.—Sparsely pubescent; glossy.

*Leaf and leaflet petiole color, upper surface*.—Close to 181A.

*Leaf and leaflet petiole color, lower surface*.—Close to 174A to 174B.

Flower description:

*Flower type and flowering habit*.—Single rotate flowers arranged on terminal compound panicles; flowers face upright, outward or downward depending on position on the inflorescence; panicles conical in shape and outwardly arching; freely and uniformly flowering habit with about 4,000 flowers developing per inflorescence and more than 100,000 flowers developing per plant during the flowering season.

*Fragrance*.—Strong; sweet and pleasant.

*Natural flowering season*.—Plants begin flowering about 13 weeks after planting; continuously flowering from late spring until late summer in The Netherlands.

*Postproduction longevity*.—Flowers last about ten days on the plant; flowers not persistent.

*Flower buds*.—Height: About 2 mm. Diameter: About 1.5 mm. Shape: Broadly elliptic. Texture and luster: Smooth, glabrous; matte. Color: Sepals, close to 157A and petals, close to NN155B slightly tinged with close to 62B.

*Inflorescence height*.—About 35.9 cm.

*Inflorescence diameter*.—About 28.9 cm.

*Flower diameter*.—About 3 mm.

*Flower depth*.—About 3 mm.

*Petals*.—Quantity per flower: Typically five in a single whorl. Length: About 2 mm. Width: About 0.4 mm. Shape: Oblanceolate. Apex: Obtuse. Base: Narrowly cuneate. Margin: Entire; not undulate. Texture and luster, upper and lower surfaces: Smooth, glabrous; matte. Color: Developing petals, upper and lower surfaces: Close to NN155D. Fully expanded petals, upper and lower surfaces: Close to NN155D; venation, close to NN155D; color does not change with development.

*Sepals*.—Calyx length: About 2 mm. Calyx diameter: About 1.5 mm. Quantity per flower: Typically five in a single whorl, lower 30% fused towards the base forming a campanulate-shaped calyx. Length: About 2 mm. Width: About 0.75 mm. Shape: Ovate. Apex: Obtuse to bluntly acute. Base: Cuneate, fused. Margin: Entire. Texture and luster, upper and lower surfaces: Smooth, glabrous; matte. Color: Developing sepals, upper and lower surfaces: Close to 155C. Fully developed sepals, upper and lower surfaces: Close to 155C to 155D.

*Peduncles*.—Length: About 35.6 cm. Diameter: About 3 mm. Angle: Mostly erect; secondary peduncles, about 40° from primary peduncle axis. Strength: Strong. Texture and luster: Moderately to densely pubescent; matte. Color: Close to 176B.

*Pedicels*.—Length: About 0.5 mm. Diameter: About 0.3 mm. Angle: About 45° from peduncle axis. Strength: Moderately strong. Texture and luster: Moderately pubescent; matte. Color: Close to 155D.

*Reproductive organs*.—Stamens: Quantity per flower: Typically ten. Filament length: About 2 mm. Filament color: Close to NN155D. Anther shape: Broadly ovate; basifixed. Anther length: About 0.2 mm. Anther diameter: About 0.2 mm. Anther color: Close to 157D. Pollen amount: Scarce. Pollen color: Close to 155A. Pistils: Quantity per flower: Two. Pistil length: About 2 mm. Stigma diameter: About 0.2 mm. Stigma shape: Club-shaped. Stigma color: Close to 155A. Style length: About 1.7 mm. Style color: Close to NN155A. Ovary color: Close to NN155A.

*Seeds and fruits*.—To date, seed and fruit development have not been observed on plants of the new *Astilbe*.

Pathogen & pest resistance: To date, plants of the new *Astilbe* have not been noted to be resistant to pathogens and pests common to *Astilbe* plants.

Garden performance: Plants of the new *Astilbe* have been observed to have good garden performance and tolerate rain, wind, temperatures ranging from about −25° to 35° C. and to be suitable for USDA Hardiness Zones 5 through 10.

It is claimed:

1. A new and distinct *Astilbe* plant named 'Moccachino' as illustrated and described.

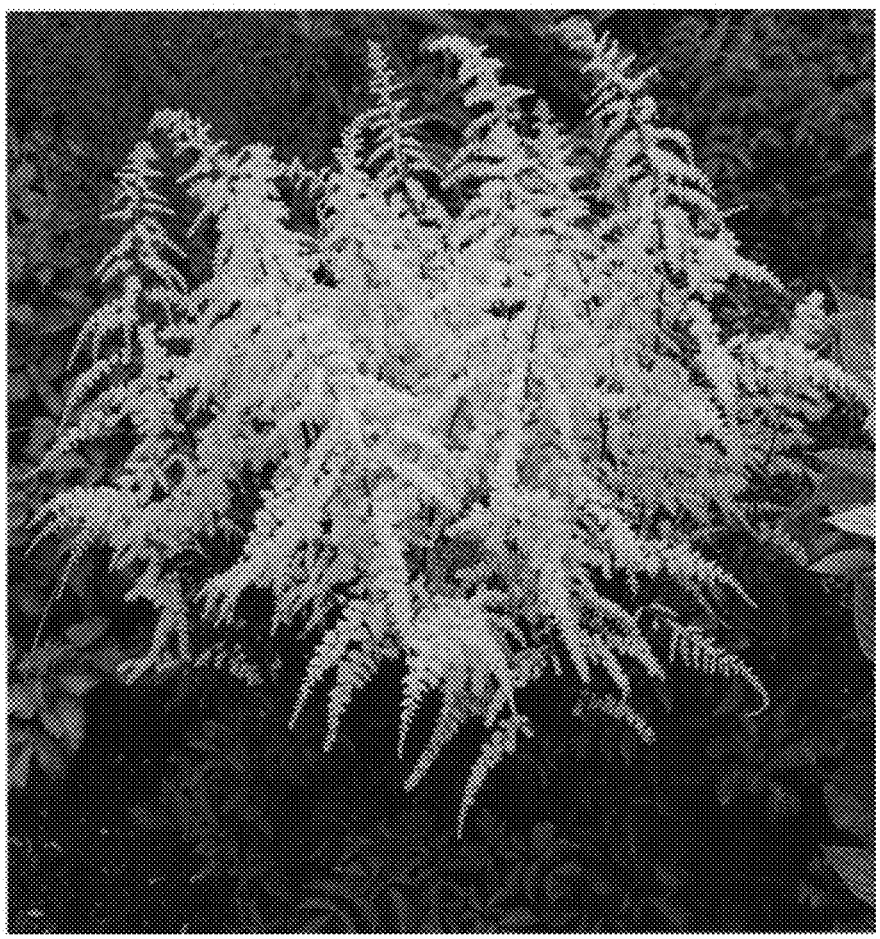

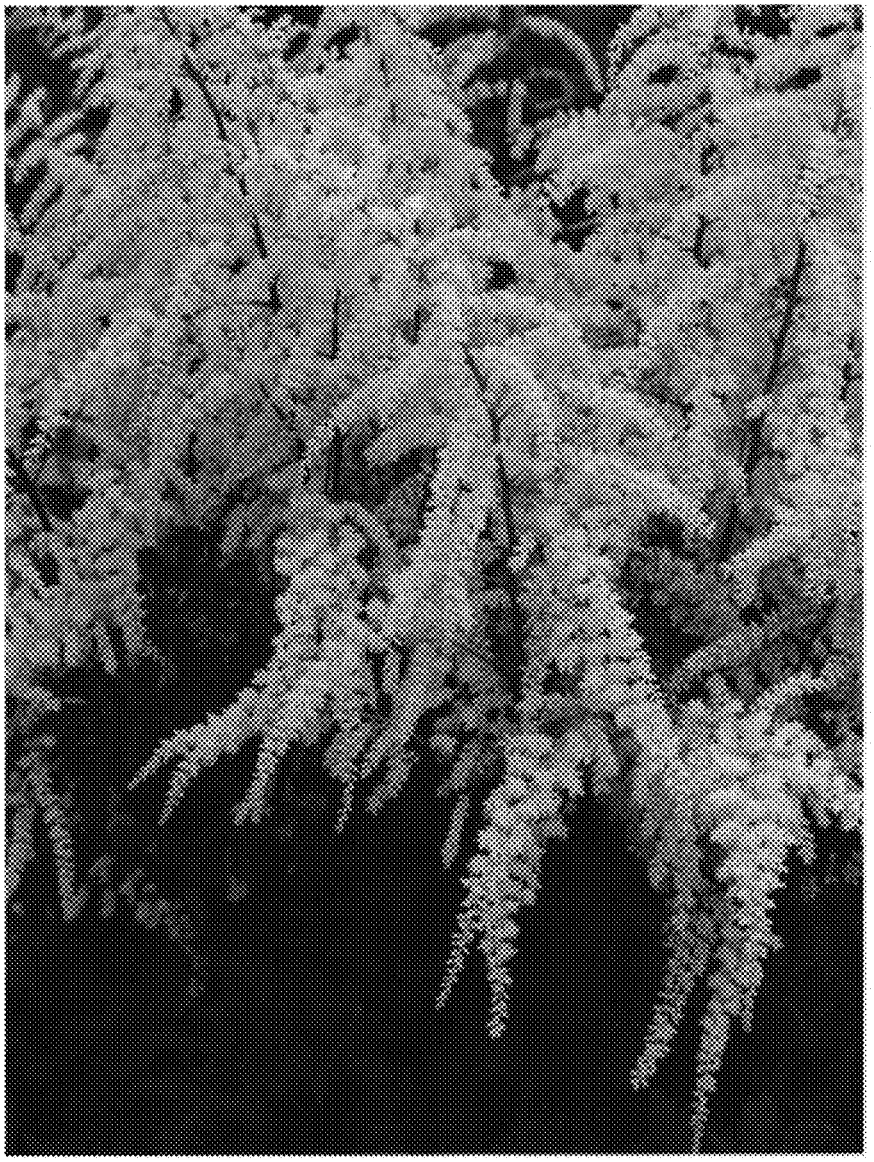

* * * * *